United States Patent
Yeo et al.

(10) Patent No.: US 9,687,498 B1
(45) Date of Patent: Jun. 27, 2017

(54) COMPOSITION FOR PREVENTING OR TREATING MUSCLE WASTING-RELATED DISEASE AND USE THEREOF

(71) Applicant: Samsung Electronics Co., Ltd., Suwon-si, Gyeonggi-do (KR)

(72) Inventors: Hyeonju Yeo, Seoul (KR); Sangchul Park, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/340,376

(22) Filed: Nov. 1, 2016

(30) Foreign Application Priority Data

Dec. 22, 2015 (KR) ........................ 10-2015-0184082

(51) Int. Cl.
*A61K 31/202* (2006.01)
*A61K 31/4418* (2006.01)
*A61K 31/7056* (2006.01)

(52) U.S. Cl.
CPC ........ *A61K 31/7056* (2013.01); *A61K 31/202* (2013.01); *A61K 31/4418* (2013.01)

(58) Field of Classification Search
None
See application file for complete search history.

(56) References Cited

U.S. PATENT DOCUMENTS 7,785,587 B2    8/2010   Whittemore et al.

OTHER PUBLICATIONS

Ruas, Cell, 151:1319 (2012).*

* cited by examiner

*Primary Examiner* — Michael Barker
(74) *Attorney, Agent, or Firm* — Leydig, Voit & Mayer, Ltd.

(57) ABSTRACT

Provided is a pharmaceutical composition for preventing or treating a muscle wasting-related disease of a subject, the composition including one or more compounds selected from the group consisting of isotretinoin, vismodegib, and lincomycin, pharmaceutically acceptable salts, stereoisomers, derivatives, or solvates thereof, or combinations thereof, and a method of preventing or treating a muscle wasting-related disease using the same.

10 Claims, 5 Drawing Sheets

VISMODEGIB

ISOTRETINOIN

LINCOMYCIN HYDROCHLORIDE

COMPOSITION FOR PREVENTING OR TREATING MUSCLE WASTING-RELATED DISEASE AND USE THEREOF

CROSS-REFERENCE TO RELATED APPLICATION

This application claims the benefit of Korean Patent Application No. 10-2015-0184082, filed on Dec. 22, 2015, in the Korean Intellectual Property Office, the entire disclosure of which is hereby incorporated by reference.

BACKGROUND

1. Field

The present disclosure relates to a composition for preventing or treating a muscle wasting-related disease of a subject, and use thereof.

2. Description of the Related Art

Muscle is an essential organ for human movement. When a reduction in proteins constituting muscle fibers or a loss of muscle fibers occurs due to aging or various pathological factors, muscle wasting or a decrease of muscle mass occurs. The muscle wasting or decrease of muscle mass may be caused by aging, malnutrition, disuse of muscles, or numerous diseases, resulting in sarcopenia, muscular atrophy, or muscle dystrophy.

In particular, one of the causes of age-related sarcopenia is an age-related decrease in the restoration of muscle injury due to constant contraction. In addition, caloric intake, reduced physical activity and hormone, or genetic factors also contribute to age-related sarcopenia. The loss of muscle associated with aging is a disease which decreases quality of life and increases the risk of death. Sarcopenia also directly causes diseases. However, the only method of preventing or treating muscle wasting or decrease of muscle mass is intake of proteins and exercise of muscle.

Accordingly, there is a demand for a drug capable of increasing muscle mass for the effective prevention or treatment of muscle wasting-related diseases.

SUMMARY

An aspect of the invention provides a pharmaceutical composition for preventing or treating a muscle wasting-related disease of a subject.

Another aspect of the invention provides a method of preventing or treating a muscle wasting-related disease.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
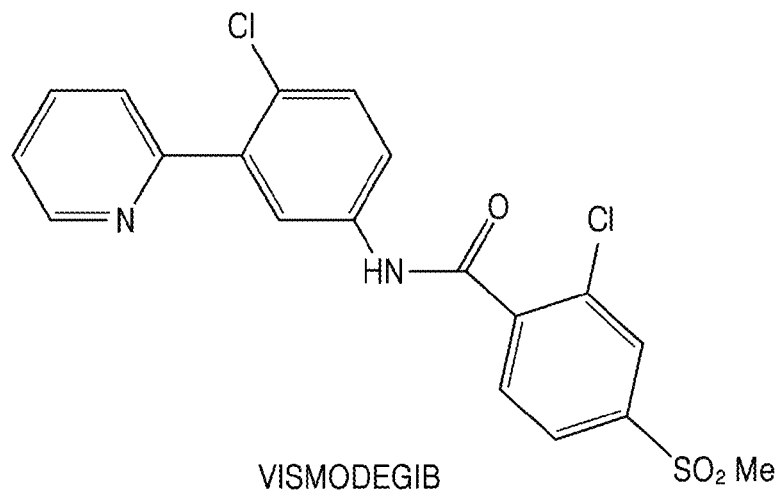
FIG. 1 shows structural formulae of selected compounds, isotretinoin, vismodegib, and lincomycin hydrochloride.
Figure 1:
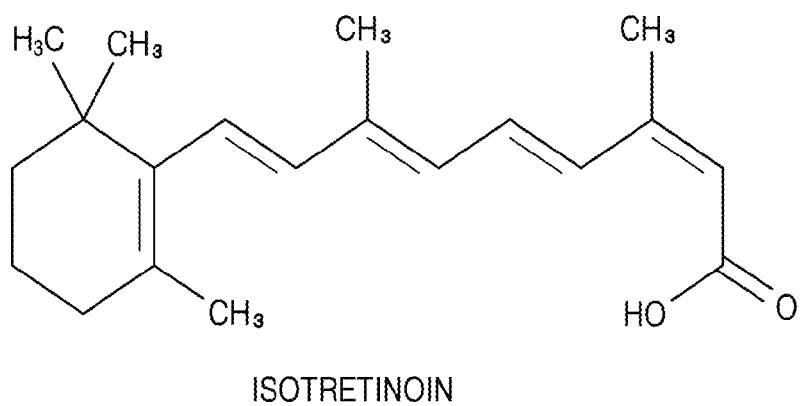
Figure 1:
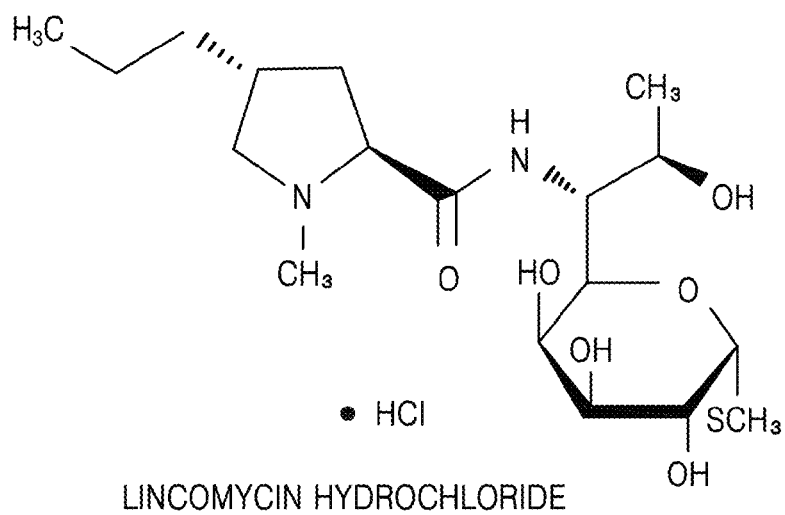

An aspect of the invention provides a pharmaceutical composition for preventing or treating a muscle wasting-related disease in a subject, the composition including one or more compounds selected from the group consisting of isotretinoin, vismodegib, and lincomycin, pharmaceutically acceptable salts, stereoisomers, derivatives, or solvates thereof, or combinations thereof (hereinafter "the active compound(s)").

Isotretinoin is (2Z,4E,6E,8E)-3,7-dimethyl-9-(2,6,6-trimethylcyclohex-1-en-1-yl)nona-2,4,6,8-tetraenoic acid. Isotretinoin is also known as 13-cis retinoic acid. Isotretinoin is known as a therapeutic agent for acne, skin cancer and neuroblastoma. Isotretinoin is marketed under the trade name of Roaccutane, Accutane, Amnesteem, Claravis, Absorica, Isotroin or Epuris.

Vismodegib is 2-chloro-N-(4-chloro-3-pyridin-2-ylphenyl)-4-methylsulfonylbenzamide. Vismodegib targets the Hedgehog signaling pathway, and is a therapeutic agent for basal-cell carcinoma (BCC). Vismodegib is marketed under the trade name of Erivedge.

Lincomycin is (2S,4R)-N-[(1R,2R)-2-hydroxy-1-[(2R,3R,4S,5R,6R)-3,4,5-trihydroxy-6-(methylsulfanyl)oxan-2-yl]propyl]-1-methyl-4-propylpyrrolidine-2-carboxamide. Lincomycin is an antibiotic produced by *Streptomyces lincolnensis*. Lincomycin inhibits protein synthesis and exhibits antibacterial activity against Gram-positive bacteria and Gram-negative cocci.

Without wishing to be bound by any particular theory or mechanism of action, it is believed the active compound(s) exert their effect by may inducing expression of peroxisome proliferator-activated receptor gamma coactivator 1-alpha 4 isoform (PGC-1α4), inhibiting expression of myostatin, or otherwise increasing the size of muscle fiber, increasing muscle mass, or exerting a combination of such effects.

PGC-1α4 is one of peroxisome proliferator-activated receptor gamma coactivator 1-alpha (PGC-1α) isoforms. PGC-1α is a transcriptional coactivator involved in the regulation of genes related to energy metabolism and a regulator of mitochondrial biogenesis. PGC-1 alpha protein provides a direct link between external physiological stimuli and the regulation of mitochondrial biogenesis, and is a major factor that regulates muscle fiber type determination. During endurance exercise, PGC-1α gene in the human skeletal muscles may be transcribed from the proximal promoter to express PGC-1α1 isoform. PGC-1α1 isoform induces myosin switching, mitochondrial biogenesis, and oxidative metabolism to decrease muscles. During muscle exercise, PGC-1α gene may be transcribed from the alternative promoter to express PGC-1α4 isoform (see Cell, vol. 151, issue 6, pp. 1319-1331, Dec. 7, 2012). PGC-1α4 isoform inhibits expression of myostatin and induces expression of insulin-like growth factor 1 (IGF-1) to cause muscle hypertrophy. PGC-1α4 may be a polypeptide encoded by the alternative promoter of PGC-1α gene in human.

Myostatin is also known as growth differentiation factor 8 (GDF-8). Myostatin is a protein produced and secreted by muscle cells that acts on muscle cells' autocrine function, and it functions to inhibit myogenesis, namely, muscle cell growth and differentiation. Myostatin may have an amino acid sequence of Genbank Accession No. NP_005250 (human) or NP_034964 (mouse). Further, myostatin may be encoded by a nucleotide sequence of Genbank Accession No. NM_005259 (human) or NM_010834 (mouse).

An increase in muscle mass may be achieved by proliferation of muscle cells, increase in the size of muscle fibers of muscle cells, or a combination thereof. The increase in the size of muscle fibers may be an increase in the diameter of muscle fibers.

Isotretinoin, vismodegib, and lincomycin, as well as pharmaceutically acceptable salts, stereoisomers, derivatives, and solvates thereof may be purchased from a commercially available source, directly synthesized using known methods, or obtained by any other technique (e.g., extraction, separation, or filtration of natural substances).

Any pharmaceutically acceptable salt may be used, such as a salt that does not cause significant irritation to an organism to which the compound is administered, and does not abrogate the biological activity and properties of the compound. The salt may be, for example, an inorganic acid salt, an organic acid salt, or a metal salt. The inorganic acid salt may be hydrochloride, bromate, phosphate, sulfate, or disulfate. The organic acid salt may be formate, acetate, propionate, lactate, oxalate, tartrate, malate, maleate, citrate, fumarate, besylate, camsylate, edisilate, trichloroaceate, trifluoroacetate, benzoate, gluconate, methanesulfonate, glycolate, succinate, 4-toluenesulfonate, galacturonate, embonate, glutamate, methane sulfonate, ethane sulfonate, benzene sulfonate, p-toluene sulfonate, or aspartate. The metal salt may be a calcium salt, a sodium salt, a magnesium salt, a strontium salt, or a potassium salt. For example, the lincomycin may be lincomycin hydrochloride. The inorganic acid salt, organic acid salt, or metal salt may be prepared according to a general method.

The compound may be in the form of a stereoisomer. The stereoisomer may be an enantiomer or a diastereomer. The compound may be a stereoisomerically pure form or a mixture of one or more stereoisomers, for example, a racemic mixture. Separation of a particular stereoisomer may be performed by one of general methods known in the art.

The active compound(s) may also be in the form of a derivative thereof. The derivative may be a compound obtained by chemically modifying a part of the compound with other atoms or atomic groups.

The active compound(s) may be in the form of a solvate. The solvate refers to a complex or aggregate formed by one or more molecules of a solute, i.e., the compound, or pharmaceutically acceptable salt, stereoisomer, or derivative thereof, and one or more molecules of a solvent. The solvate may be a complex or aggregate formed with, for example, water, methanol, ethanol, isopropanol, or acetic acid. The solvate may be, for example, hydrate.

The subject may be a mammal, for example, human, cow, horse, pig, dog, sheep, goat, or cat. The subject may be a subject having muscle wasting-related disease or at risk of having muscle wasting-related disease.

Muscle wasting-related diseases (muscle wasting diseases) include diseases with pathological muscle wasting and natural muscle wasting. The muscle wasting may be gradual loss of muscle mass, or weakness or degeneration of muscles, in particular, skeletal muscles, voluntary muscles, and heart muscles. The muscle wasting may be attributed to any of a variety of factors including genetic predispositions; age-related diseases such as hypertension, impaired glucose tolerance, diabetes, obesity, dyslipidemia, atherosclerosis, and cardiovascular diseases; chronic diseases such as cancers, autoimmune diseases, infectious diseases, AIDS, chronic inflammatory diseases, arthritis, malnutrition, renal diseases, chronic obstructive pulmonary disease, pulmonary emphysema, rachitis, chronic lower spine pain, peripheral nerve injury, central nerve injury, and chemical injury; conditions such as long-term immobilization, ineffectualness-like conditions such as bone fracture or trauma, and post-surgery bed rest; and the progressive decrease in skeletal muscle mass and strength caused by aging processes.

In some embodiments, the muscle wasting-related disease may be sarcopenia, muscular atrophy, muscle dystrophy, or a combination thereof.

Sarcopenia refers to a symptom caused by a decrease in skeletal muscle mass, and includes a pathological decrease in muscle mass and a natural decrease in muscle mass. Sarcopenia may be age-related sarcopenia, diabetes-related sarcopenia, obesity-related sarcopenia, or a combination thereof. Age-related sarcopenia is a decline in muscle mass with aging, and it may be also called sarcopenia caused by aging.

Muscular atrophy refers to a partial or complete loss of muscle mass. Muscle dystrophy is a muscle disease involving progressive muscle weakness and atrophy and death of muscle cells and tissues. Muscle atrophy may include diseases or conditions accompanied by, for example, muscle weakness accompanied by muscle atrophy, in particular, a decrease in muscle mass or muscle weakness of proximal muscles, a decrease in muscle function, a decrease of muscle mass, etc. Muscular atrophy or muscle dystrophy may be muscular atrophy caused by long-term bed rest, muscular atrophy caused by an assistive device for therapy, or muscular atrophy caused by cachexia, amyotrophic lateral sclerosis, spinal progressive muscular atrophy, muscular dystrophy, or a combination thereof.

In some embodiments, the muscle wasting-related disease may be associated with reduced PGC-1α4 expression compared to a normal control that does not have a muscle wasting-related disease.

The term "prevention" of a muscle wasting-related disease encompasses inhibition of any symptom or physiologic response of the muscle wasting-related disease or delayed onset of any symptom or physiologic response of the muscle wasting-related disease. The term "treatment" of a muscle wasting-related disease encompasses any degree of amelioration of any physiological response or symptom brought on by a muscle wasting-related disease.

The pharmaceutical composition may include the active compound(s), in a "therapeutically effective amount". In the pharmaceutical composition, "therapeutically effective amount" refers to an amount sufficient to exhibit a therapeutic effect when administered to a subject in need of treatment. The effective amount may be determined depending on the severity of disease, a patient's age, body weight, health conditions, gender, drug sensitivity, administration time, administration route, excretion rate, treatment period, drugs blended with or co-administered with the composition, and other factors well known in the medical field. The "effective amount" may be about 10 mg to about 10 g, about 50 mg to about 9 g, about 100 mg to about 8 g, about 200 mg to about 7 g, about 300 mg to about 6 g, about 400 mg to about 5 g, about 500 mg to about 4 g, about 500 mg to about 3 g, about 500 mg to about 2 g, or about 500 mg to about 1 g, based on the composition.

The pharmaceutical composition may further include a pharmaceutically acceptable carrier. In the pharmaceutical composition, the "pharmaceutically acceptable carrier" refers to a substance used in combination with an active ingredient to aid application of the active ingredient, and generally, refers to an inert material. The carrier includes general pharmaceutically acceptable excipients, additives, or diluents. The carrier includes one or more selected from the group consisting of, for example, a filler, a binder, a disintegrant, a buffering agent, a preservative, an antioxidant, a lubricant, a flavoring agent, a thickener, a coloring agent, an emulsifier, a suspension, a stabilizer, and an isotonic agent. The carrier may include, for example, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, or mineral oils.

The pharmaceutical composition may further include one or more additional active ingredients for the prevention or treatment of muscle wasting-related disease.

The pharmaceutical composition may have a formulation for oral or parenteral administration. The pharmaceutical composition may be formulated in various forms including granules, tablets, capsules, aqueous solutions, or suspensions. In the case of tablet formulation for oral use, an excipient such as lactose or corn starch, and a lubricant such as magnesium stearate, may be generally added to the composition. In the case of capsule formulation for oral use, lactose and/or dry corn starch may be used as a diluent. When an aqueous suspension for oral use is required, an active ingredient may be used in combination with an emulsifier and/or a suspending agent. If necessary, a particular sweetening agent and/or a flavoring agent may be added. In the case of intramuscular, intraperitoneal, subcutaneous, and intravenous administration, a sterile solution of an active ingredient is generally prepared, thereby appropriately adjusting and buffering the pH of the solution. In the case of intravenous administration, the total concentration of solutes is adjusted to render the formulation isotonicity. The pharmaceutical composition may be prepared as an aqueous solution containing a pharmaceutically acceptable carrier having a pH of 7.4 as of brine. The solution may be introduced into muscles of a patient by local bolus injection.

The pharmaceutical composition may be administered orally or administered parenterally in a way of intravenous, intraperitoneal, subcutaneous, intramuscular, rectal, and topical administration. An administration dose of the pharmaceutical composition may be, for example, in the range of about 0.001 mg/kg to about 100 mg/kg, about 0.01 mg/kg to about 10 mg/kg, or about 0.1 mg/kg to about 1 mg/kg per adult once a day, several times a day, once every two days, twice every few days, once a week, or once a month to once a year.

Another aspect provides a method of preventing or treating a muscle wasting-related disease, the method including administering to a subject one or more compounds selected from the group consisting of isotretinoin, vismodegib, and lincomycin, pharmaceutically acceptable salts, stereoisomers, derivatives, or solvates thereof, or combinations thereof. All aspects of the method, including the isotretinoin, vismodegib, lincomycin, pharmaceutically acceptable salt, stereoisomer, derivative, solvate, subject, muscle wasting-related disease, prevention, and treatment, are the same as described above with respect to the pharmaceutical composition and its use.

The administration may be performed in the dose range of about 0.001 mg/kg to about 100 mg/kg per adult once a day, several times a day, once every two days, twice every few days, once a week, or once a month to once a year during a period of one day to 1 year. The administration may be performed by a method known in the art. The composition may be administered directly to a subject by any means such as oral, intramuscular, intravenous, intraperitoneal, subcutaneous, transdermal, rectal, and topical administration. The administration may be topical or systemic administration.

According to the pharmaceutical composition for preventing or treating a muscle wasting-related disease of a subject, including one or more compounds selected from the group consisting of isotretinoin, vismodegib, and lincomycin, pharmaceutically acceptable salts, stereoisomers, derivatives, or solvates thereof, or combinations thereof, and the method of preventing or treating the muscle wasting-related disease using the same, the size of muscle fibers or mass of muscles may be increased, thereby effectively preventing or treating the muscle wasting-related disease.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, the present invention will be described in more detail with reference to Examples. However, these Examples are for illustrative purposes only, and the scope of the invention is not intended to be limited by these Examples.

Example 1

Screening of Compounds Inducing Muscle Mass Increase and Verification of Effects Thereof 1. Screening of Compounds Selected were compounds which increase muscle mass, increase expression of PGC-1 alpha 4 isoform known as a major factor for muscle hypertrophy, and inhibits muscle cells and differentiations to inhibit expression of myostatin.

In detail, C2C12 cell line (mouse gastrocnemius muscle, ATCC® CRL-1772™) was seeded in a 10% FBS/DMEM culture medium. When the cells reached about 70% confluence in 5% $CO_2$ incubator at 37° C., the culture medium was replaced by 2% FBS/DMEM, and further cultured for about 4 days to induce complete differentiation into muscle cells. The C2C12 cell line is a mouse myoblast cell line obtained through continuous culture of myoblasts cultured from the gastrocnemius muscle of C3H mice.

When the C2C12 cells were completely differentiated, the medium was removed, and 10 μM (in 0.1% DMSO) of active compound for screening was added to the cultured muscle cells, followed by incubation under conditions of 37° C. and 5% $CO_2$ for about 24 hours. As the active compound for screening, a library of a total of 700 compounds (Selleck Chemicals) was used. Thereafter, the cultured muscle cells were washed with PBS to obtain muscle cells. As a negative control, muscle cells treated with DMSO (Sima-Aldrich), instead of the active compound for screening, were used. As a positive control, muscle cells treated with forskolin were used. Forskolin is known to increase expression of PGC-1 alpha 4 isoform.

Total RNA was separated according to the manufacturer's protocol by adding a Trizol reagent (Invitrogen) to the obtained cells. cDNA was synthesized from the separated total RNA using reverse transcriptase. The mRNA levels of PGC-1 alpha 4 isoform and myostatin were quantified using a real time PCR (MyiQPCR instrument, BioRad), which is a device for measuring SYBR Green. The resulting amounts were then normalized to the amount of GAPDH mRNA.

After normalization of the values obtained from the amplification to GAPDH gene, relative mRNA expression levels of PGC-1 alpha 4 isoform and myostatin were quantified. The relative mRNA expression levels (Arbitrary Unit; AU) of PGC-1 alpha 4 isoform and myostatin thus quantified are shown in FIGS. 2A and 2B, respectively (*: p<0.05 vs. negative control).

Compounds increasing the level of PGC-1 alpha 4 isoform and decreasing the level of myostatin, compared to the negative control, were selected. The selected compounds were isotretinoin, vismodegib, and lincomycin hydrochloride (FIG. 1).

Figure 2A:
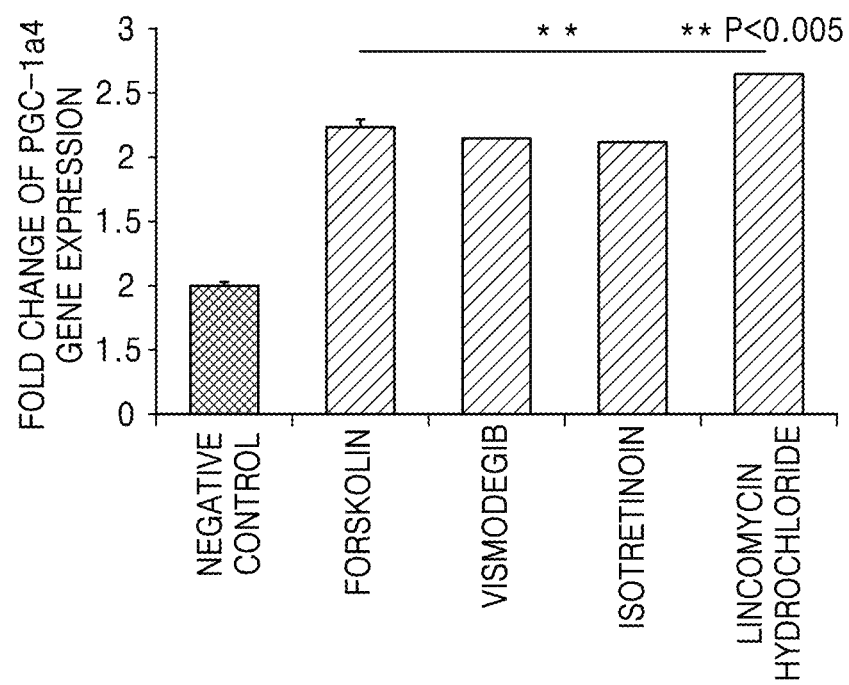
FIGS. 2A and 2B are graphs showing the expression level of PGC-1 alpha 4 isoform (FIG. 2A) and myostatin (FIG. 2B) in C2C12 cells, which were increased by treatment with the selected compounds (relative to a negative control group)
Figure 2B:
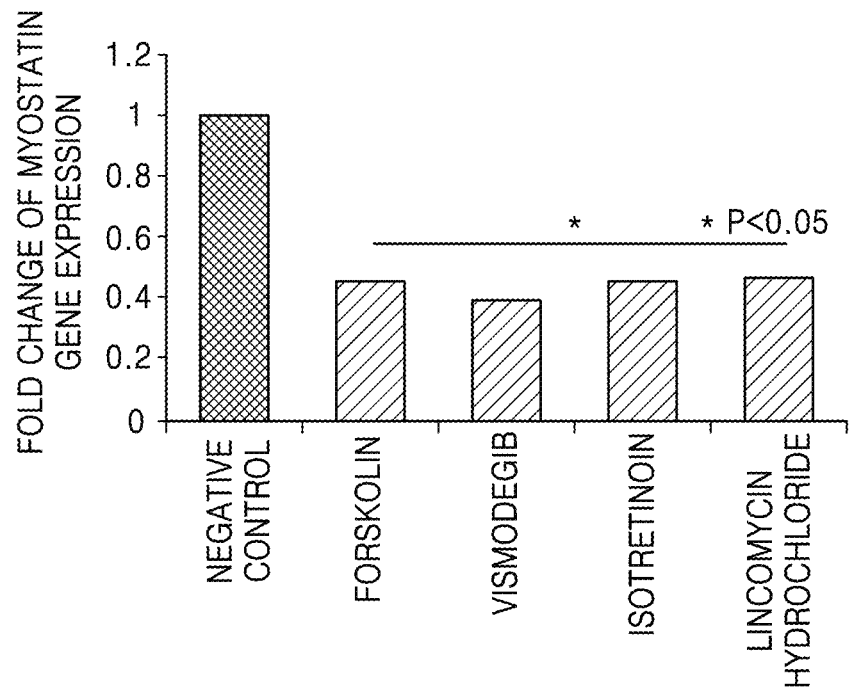

Expression rates of PGC-1 alpha 4 isoform and myostatin increased by the selected compounds, compared to the negative control, were calculated, and each of them is shown in FIGS. 2A and 2B. As shown in FIGS. 2A and 2B, it was confirmed that the selected compounds increase expression of PGC-1 alpha 4 isoform and decrease expression of myostatin, thereby preventing or treating muscle loss.

2. Muscle Fiber-Protecting Effect of Selected Compounds

Muscle fiber-protecting effects of the compounds selected in 1. were examined by measuring the diameter of muscle fiber according to addition of the selected compounds.

As described in Example 1.1, C2C12 cells were completely differentiated to muscle cells. After removal of the medium, 4 ml of a fresh medium containing each 100 µM of isotretinoin (Roche), vismodegib (Genentech), or lincomycin hydrochloride (Sima-Aldrich) was added, and the cells were cultured in a 5% $CO_2$ incubator at 37° C. for about 24 hours. As a negative control, muscle cells treated with DMSO (Sima-Aldrich), instead of the selected compounds, were used. As a positive control, muscle cells treated with forskolin were used.

Thereafter, the cultured cells were washed with PBS. Muscle fibers of the cells were photographed with a microscope (×200), and diameter (µm) of the muscle fiber was measured. An image of the muscle fibers is shown in FIG. 3A and the measured diameter of muscle fibers is shown in FIG. 3B.

Figure 3A:
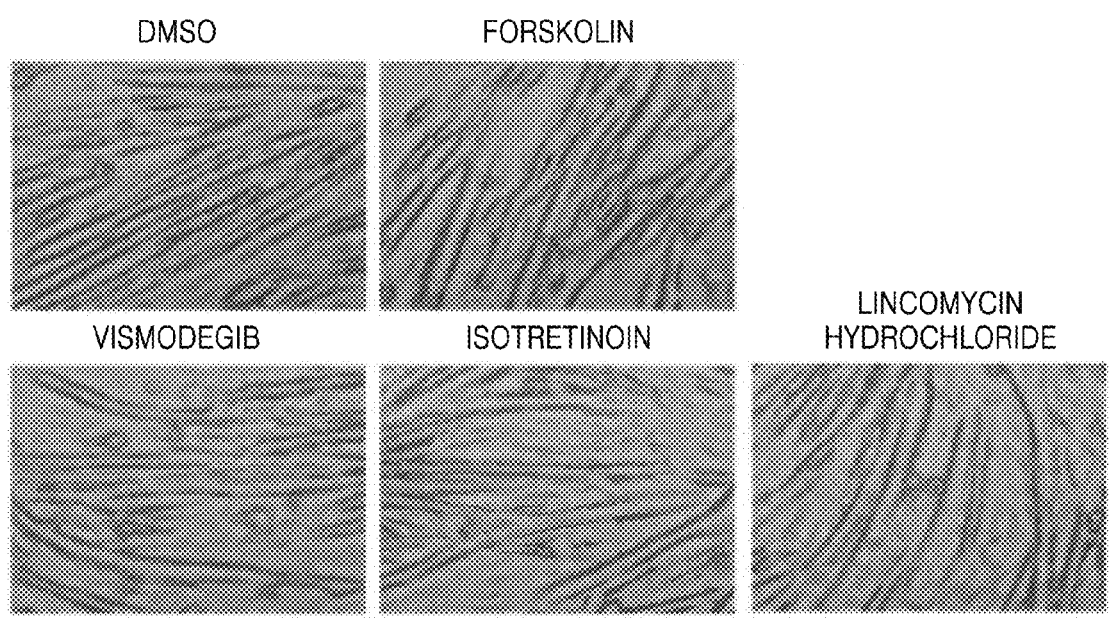
FIGS. 3A and 3B provide images (FIG. 3A) showing muscle fibers of muscles cells, and a graph (FIG. 3B) showing a diameter (μm) of the muscle fiber after culturing the muscles cells in the presence of the respective selected compounds, respectively.
Figure 3B:
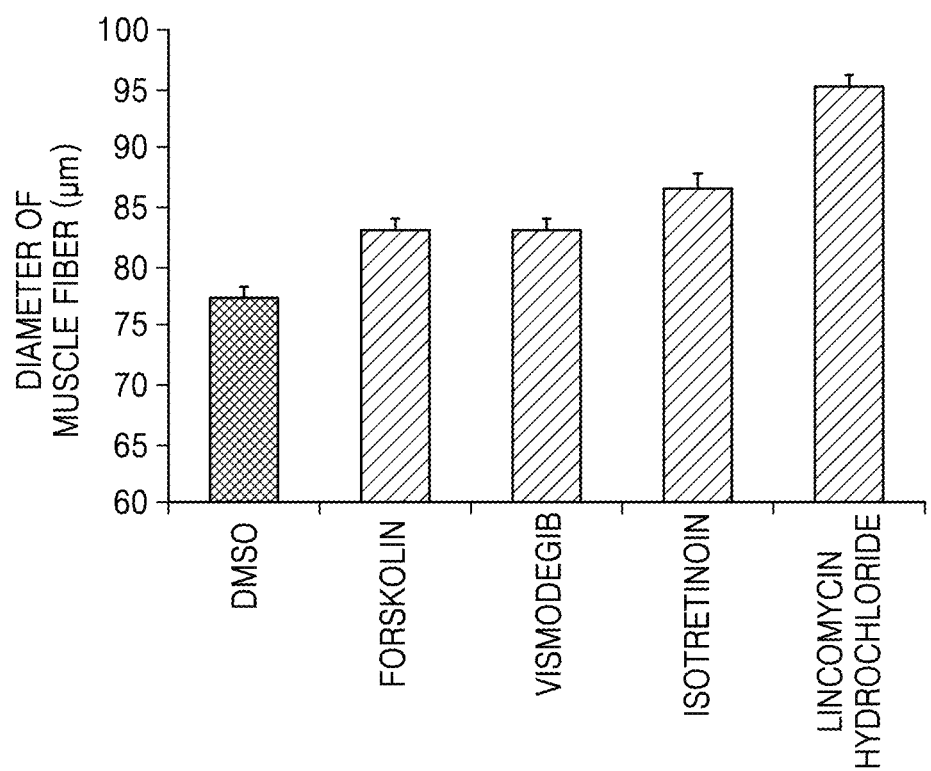

As shown in FIGS. 3A and 3B, when the muscle cells were treated with isotretinoin, vismodegib, or lincomycin hydrochloride, the muscle fiber diameter was increased, compared to the negative control, and the muscle fiber diameter was similar to or higher than that of the positive control, forskolin. Consequently, it was confirmed that isotretinoin, vismodegib, or lincomycin hydrochloride increases muscle mass, and is expected to be useful prevent or treat sarcopenia and muscular atrophy in a subject.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of preventing or treating a muscle wasting disease, the method comprising administering to a subject afflicted with a muscle wasting disease one or more compounds selected from the group consisting of isotretinoin, vismodegib, and lincomycin, a pharmaceutically acceptable salt thereof, stereoisomer thereof, solvate thereof, or combination thereof.

2. The method of claim 1, wherein the subject is a subject having muscle wasting-related disease or at the risk of having muscle wasting-related disease.

3. The method of claim 1, wherein the administration is performed to achieve induction of peroxisome proliferator-activated receptor gamma coactivator 1-alpha 4 isoform (PGC-1α4) expression, inhibition of myostatin expression, increase of muscle fiber size, increase of muscle mass, or a combination thereof.

4. The method of claim 1, wherein the licomycin is licomycin hydrochloride.

5. The method of claim 1, wherein the muscle wasting disease is sarcopenia, muscular atrophy, muscle dystrophy, or a combination thereof.

6. The method of claim 5, wherein the muscle wasting disease is age-related sarcopenia, diabetes-related sarcopenia, obesity-related sarcopenia, or a combination thereof.

7. The method of claim 5, wherein the muscle wasting disease is muscular atrophy caused by long-term bed rest, muscular atrophy caused by an assistive device for therapy, muscular atrophy caused by cachexia, amyotrophic lateral sclerosis, spinal progressive muscular atrophy, muscular dystrophy, or a combination thereof.

8. The method of claim 1, wherein the one or more compounds selected from the group consisting of isotretinoin, vismodegib, lincomycin, pharmaceutically acceptable salt thereof, stereoisomer thereof, solvate thereof, or combination thereof are administered in an amount of 0.001 mg to 100 mg per body weight (kg) of the subject.

9. The method of claim 1, wherein the one or more compounds selected from the group consisting of isotretinoin, vismodegib, lincomycin, pharmaceutically acceptable salt thereof, stereoisomer thereof, solvate thereof, or combination thereof are administered via oral, intravenous, intramuscular, oral, transdermal, mucosal, intranasal, intratracheal, or subcutaneous route.

10. The method of claim 1, wherein the one or more compounds selected from the group consisting of isotretinoin, vismodegib, lincomycin, pharmaceutically acceptable salt thereof, stereoisomer thereof, solvate thereof, or combination thereof is are administered once a day, more than once a day, once every two days, once a week, or once a month to once a year during a period of one day to 1 year.

* * * * *